United States Patent [19]

Sanger et al.

[11] Patent Number: 5,063,231

[45] Date of Patent: Nov. 5, 1991

[54] METHOD OF TREATMENT OF VISCERAL PAIN

[75] Inventors: Gareth J. Sanger; Helen E. Marr, both of Harlow, England

[73] Assignee: Beecham Group p.l.c., Harlow, England

[21] Appl. No.: 520,108

[22] Filed: May 7, 1990

Related U.S. Application Data

[62] Division of Ser. No. 348,051, May 2, 1989, Pat. No. 4,942,160, which is a division of Ser. No. 145,537, Jan. 19, 1988, Pat. No. 4,845,092.

[51] Int. Cl.$^5$ .................. A61K 31/55; A61K 31/44; A61K 31/40
[52] U.S. Cl. .................. 514/214; 514/216; 514/299; 514/305; 514/412; 514/413
[58] Field of Search ............... 514/216, 214, 305, 299, 514/412, 413

[56] References Cited

FOREIGN PATENT DOCUMENTS 0235878 9/1987 European Pat. Off. .

OTHER PUBLICATIONS

Chemical Abstracts (109: 73321j), 1988.

Primary Examiner—Frederick E. Waddell
Assistant Examiner—Kevin Weddington
Attorney, Agent, or Firm—Hopgood, Calimafde, Kalil, Blaustein & Judlowe

[57] ABSTRACT

A method of treatment of visceral pain in mammals, including humans, which method comprises the administration to the mammal in need of such treatment, an effective amount of a compound of formula (I) or a pharmaceutically acceptable salt thereof:

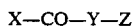

X—CO—Y—Z       (I)

wherein
X is a group of formula (a), (b), (c), (d) or (e):

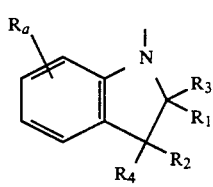

(a)

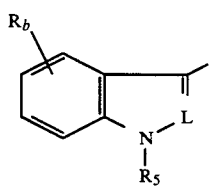

(b)

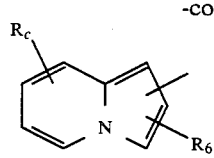

(c)

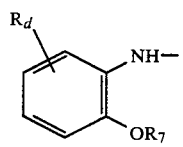

(d)

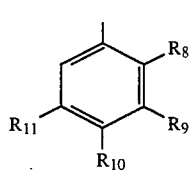

(e)

wherein
$R_a$ to $R_d$ are selected from hydrogen, halogen or hydroxy;
$R_1$ is hydrogen and $R_2$ is hydrogen or $C_{1-4}$ alkyl; or
$R_1$ and $R_2$ together are a bond;
$R_3$ to $R_7$ are independently hydrogen or $C_{1-6}$ alkyl; and
$R_4$ together with $R_2$ may be $C_{2-7}$ polymethylene when $R_1$ is hydrogen; either $R_8$ is $C_{1-6}$ alkoxy;
$R_9$ is hydrogen;
$R_{10}$ is amino or $C_{1-7}$ alkanoylamino; and
$R_{11}$ is halo or $C_{1-6}$ alkylthio; or
$R_8$ is hydrogen;
$R_9$ is halo, $C_{1-6}$ alkoxy or $C_{1-6}$ alkyl;
$R_{10}$ is hydrogen or $C_{1-6}$ alkoxy; and
$R_{11}$ is halo, $C_{1-6}$ alkoxy or $C_{1-6}$ alkyl;
L is CH or N;
Y is NH or O, with the proviso that Y is NH when X is (e) and $R_8$ is $C_{1-6}$ alkoxy;
Z is a group of formula (f), (g) or (h):

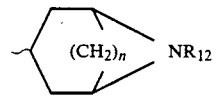

(f)

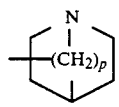

(g)

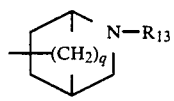

(h)

wherein
n is 2 or 3;
p and q are independently 1 to 3; and
$R_{12}$ or $R_{13}$ is methyl or ethyl.

2 Claims, No Drawings

METHOD OF TREATMENT OF VISCERAL PAIN

This application is a division of copending U.S. patent application Ser. No. 348,051 filed May 2, 1989, now U.S. Pat. No. 4,942,160 which in turn is a division of U.S. Ser. No. 145,537 filed Jan. 19, 1988, now U.S. Pat. No. 4,845,092.

This invention relates to a method of treatment of visceral pain in mammals, including humans, and to the use of compounds in the preparation of a medicament for the treatment of visceral pain.

GB 2125398A, EP-A-200444, EP-A-247266, EP-A-235878, European patent Application No. 87306548.6, EP-A-67770, EP-A-158265 and EP-A-158532 disclose classes of compounds which are 5-HT$_3$ receptor antagonists useful in the treatment of inter alia migraine, cluster headache, trigeminal neuralgia and emesis.

It has now been discovered that certain 5-HT3 receptor antagonists, such as the above classes of compounds, are potentially useful in the treatment of visceral pain.

Visceral pain is caused by abnormal distension of hollow visceral organs. In particular, inflation of the colon of patients with irritable bowel syndrome will induce pain in various sites throughout the abdomen, mimicking the disease symptoms (Latimer et al, 1979, J. Behav. Med., 2, 285–295).

Accordingly, the present invention provides a method of treatment of visceral pain in mammals, including humans which method comprises the administration to the mammal in need of such treatment, an effective amount of a compound of formula (I) or a pharmaceutically acceptable salt thereof:

X—CO—Y—Z    (I)

wherein
X is a group of formula (a), (b), (c), (d) or (e):

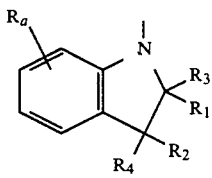
(a)

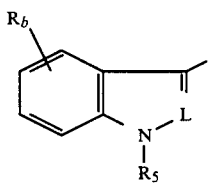
(b)

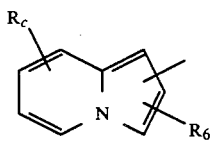
(c)

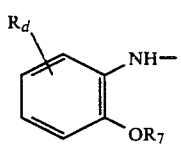
(d)

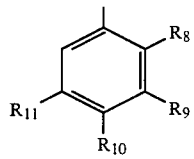
(e)

wherein
R$_a$ to R$_d$ are selected from hydrogen, halogen or hydroxy;
R$_1$ is hydrogen and R$_2$ is hydrogen or C$_{1-4}$ alkyl; or
R$_1$ and R$_2$ together are a bond;
R$_3$ to R$_7$ are independently hydrogen or C$_{1-6}$ alkyl; and
R$_4$ together with R$_2$ may be C$_{2-7}$ polymethylene when R$_1$ is hydrogen;
either R$_8$ is C$_{1-6}$ alkoxy;
R$_9$ is hydrogen;
R$_{10}$ is amino or C$_{1-7}$ alkanoylamino; and
R$_{11}$ is halo or C$_{1-6}$ alkylthio; or
R$_8$ is hydrogen;
R$_9$ is halo, C$_{1-6}$ alkoxy or C$_{1-6}$ alkyl;
R$_{10}$ is hydrogen or c$_{1-6}$ alkoxy; and
R$_{11}$ is halo, C$_{1-6}$ alkoxy or C$_{1-6}$ alkyl;
L is CH or N;
Y is NH or O, with the proviso that Y is NH when X is (e) and R$_8$ is C$_{1-6}$ alkoxy;
Z is a group of formula (f), (g) or (h):

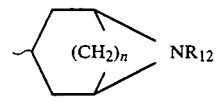
(f)

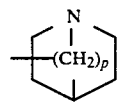
(g)

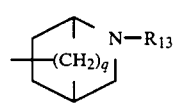
(h)

wherein
n is 2 or 3;
p and q are independently 1 to 3; and
R$_{12}$ or R$_{13}$ is methyl or ethyl.

Examples of moieties in alkyl or alkyl containing groups in R$_1$ to R$_{11}$ include methyl, ethyl, n- and iso-propyl, n-, iso-, sec- and tert-butyl, preferably methyl.

Suitable examples of R$_2$ and R$_4$ when joined include C$_2$, C$_3$, C$_4$, C$_5$ or C$_6$ polymethylene, preferably C$_2$, C$_3$, C$_4$ or C$_5$ polymethylene.

R$_a$ to R$_d$ are preferably selected from hydrogen, fluoro, chloro and hydroxy, most preferably hydrogen.

R$_b$ may be 5-, 6- or 7-chloro or fluoro.

When X is of sub-formula (a), R$_1$ and R$_3$ are preferably both hydrogen and one or both of R$_2$ and R$_4$ (most preferably both) are alkyl groups, such as methyl, or are joined to form C$_{2-7}$ polymethylene; or when one of R$_2$ and R$_4$ is hydrogen, the other is preferably ethyl or n- or iso- propyl.

When X is of sub-formula (b), R$_5$ is preferably hydrogen or a methyl or ethyl group.

When X is of sub-formula (c), one of CO—Y—Z and $R_6$ is attached at the 1-position and the other is attached at the 3-position as depicted in sub-formula (c), and $R_6$ is preferably methyl or ethyl.

When X is of sub-formula (d), $R_7$ is preferably methyl.

When X is of sub-formula (e), and $R_8$ is $C_{1-6}$ alkoxy, $R_8$ is preferably methoxy, $R_{10}$ is preferably amino and $R_{11}$ is preferably chloro or bromo, most preferably chloro.

When X is of sub-formula (e), and $R_8$ is hydrogen, $R_9$ and $R_{11}$ are preferably chloro or methyl and $R_{10}$ is preferably hydrogen.

X is preferably a group of formula (b) and L is preferably N.

Y is preferably NH.

When Z is a group of sub-formula (f), n is 2 or 3, preferably 3 when X is of sub-formula (b) wherein L is N.

When Z is a group of sub-formula (g) or (h), p and q are preferably 1 or 2.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, lactic, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid. Preferably the acid addition salt is the hydrochloride salt.

Pharmaceutically acceptable salts also include quaternary derivatives, examples of which include the compounds quaternised by compounds such as $R_{20}$-T wherein $R_{20}$ is $C_{1-6}$ alkyl, phenyl-$C_{1-6}$ alkyl or $C_{5-7}$ cycloalkyl, and T is a radical corresponding to an anion of an acid. Suitable examples of $R_{20}$ include methyl, ethyl and n- and iso-propyl; and benzyl and phenethyl. Suitable examples of Z include halide such as chloride, bromide and iodide.

Pharmaceutically acceptable salts also include internal salts such as pharmaceutically acceptable N-oxides.

The compounds of the formula (I), and their pharmaceutically acceptable salts may also form pharmaceutically acceptable solvates, such as hydrates which are included whereever a compound of formula (I) or a salt thereof is herein referred to.

It will of course be realised that some of the compounds of the formula (I) have chiral or prochiral centres, and thus are capable of existing in a number of stereoisomeric forms, including enantiomers. The invention extends to each of these stereoisomeric forms (including enantiomers), and to mixtures thereof (including racemates). The different stereoisomeric forms may be separated one from the other by the usual methods.

Compounds of the formula (I) and their salts may be prepared in accordance with the methods described in the abovementioned UK and European Patent references, the subject matter of which are incorporated herein by reference.

The administration of the compound of formula (I) or a pharmaceutically acceptable salt thereof may be by way of oral or parenteral administration.

An amount effective to treat the disorders hereinbefore described depends on the relative efficacies of the compounds of the invention, the nature and severity of the disorder being treated and the weight of the mammal. However, a unit dose for a 70kg adult will normally contain 0.1 to 100mg for example 0.2 to 50 mg, of the compound of formula (I) or a pharmaceutically acceptable salt thereof. Unit doses may be administered once or more than once a day, for example, 2, 3 or 4 times a day, more usually 1 to 3 times a day, that is in the range of approximately 0.0002 to 5 mg/kg/day, more usually 0.0004 to 2.5 mg/kg/day.

No adverse toxicological effects are indicated at any of the aforementioned dosage ranges.

It is preferred that the compound of formula (I) or a pharmaceutically acceptable salt thereof is administered in the form of a unit dose pharmaceutical composition in which is combined with a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of lycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound.

The present invention also provides the use of a compound of formula (I) or a pharmaceutically acceptable salt thereof in the preparation of a medicament for use in the treatment of visceral pain in mammals, including humans. Such treatment may be carried out in the manner as hereinbefore described.

The present invention further provides a pharmaceutical composition for use in the treatment of visceral pain which comprises an effective amount of a compound of formula (I) or a pharmaceutically acceptable salt thereof and a pharmaceutically acceptable carrier. Such compositions may be prepared in the manner as hereinbefore described.

The following pharmacological data illustrate the invention.

Compound E6 is the Compound of Example 6 of EP-A-200444, N-(endo-9-methyl-9-azabicyclo[3.3.1]-non-3-yl)-1-methyl-indazole-3-carboxamide monohydrochloride (also known as BRL 43694A).

ICS 205-930 is the Compound of Example A-2 of GB 2125398A, -indol-3-yl carboxylic acid (endo-8-methyl-8-azabicyclo[3.2.1]oct-3-yl)ester.

Compound E5 is the Compound of Example 5 of EP-A-247266, endo-N-(8-methyl-8-azabicyclo[3.2.1]oct-3-yl)-2,3-dihydro-3,3-dimethylindole-1-carboxamide.

PHARMACOLOGICAL DATA

Visceral pain in man or in animals is associated with a range of pseudoaffective, pain-related responses which are easily monitored. For example, distension of anaesthetised rat ileum induces a fall in blood pressure which can be blocked by morphine or by capsaicin, indicating that it is part of the pain reflex (Lembeck and Skofitsch, 1982, Naunyn-Schmiedeberg's Arch. Pharmac., 321, 179–183). Furthermore, nociceptive stimuli directed to the intestine can reflexely suppress gastric motility (Abrahamsson et al, 1979, Scand. J. Gastroenterol., 14, 101–106). Compounds which selectively block such pseudoaffective responses may therefore prevent both visceral pain (e.g. pain associated with the irritable bowel syndrome, gall stones, kidney stones, etc.) and the paralytic ileus (suppression of gastrointestinal motility) associated with abdominal surgery.

METHOD

Rats were prepared under urethane anaesthesia for measurement of blood pressure via a cannula in the carotid artery. The whole stomach was intubated with a cannula down the oesophagus and ligated distal to the pyloric sphincter before being filled with 5 ml saline. A 3–4 cm segment of the duodenum was isolated immediately below the stomach. This segment was connected orally to saline-filled pressure reservoirs with drainage occurring aborally. Distension of the duodenum with a pressure of 75 cm $H_2O$ induced a fall in blood pressure and a fall in intragastric pressure, which could be repeated over a series of distensions. Intravenous (i.v.) injection of E6 10 $\mu g$ $kg^{-1}$ reduced both the fall in blood pressure and intragastric pressure caused by duodenal distension.

The results are shown in Tables 1 to 3.

TABLE 1

Inhibition by E6 of the fall in blood pressure and intragastric pressure induced by duodenal distension in the anaesthetised rat

| | % Inhibition of fall in blood pressure | % Inhibition of fall in intragastric pressure |
|---|---|---|
| Time (min) after administration of E6 1 μg/kg (n = 6) | | |
| 5 | 34 ± 16 | 19 ± 8 |
| 10 | 37 ± 14* | 0 ± 13 |
| 15 | 32 ± 14 | 10 ± 11 |
| 20 | 35 ± 16 | 9 ± 9 |
| Time (min) after administration of E6 10 μg/kg (n = 9) | | |
| 5 | 2 ± 17 | 23 ± 10 |
| 10 | 37 ± 8*** | 49 ± 15** |
| 15 | 47 ± 14** | 66 ± 15*** |
| 20 | 56 ± 8*** | 74 ± 14*** |

*$P < 0.05$;
**$P < 0.01$;
***$P < 0.005$
Student's 't' test

TABLE 2

Inhibition by ICS 205-930 of the fall in blood pressure and intragastric pressure induced by duodenal distension in the anaesthetised rat

| Time (min) after administration of ICS 205-930 100 μg/kg | % Inhibition of fall in blood pressure (n = 5) | % Inhibition of fall in intragastric pressure (n = 4) |
|---|---|---|
| 5 | 8 ± 27 | 5 ± 13 |
| 10 | 33 ± 7** | 37 ± 6** |
| 15 | 47 ± 18 | 46 ± 8** |
| 20 | 45 ± 16* | 27 ± 20 |

*$P < 0.05$;
**$P < 0.01$
Student's 't' test

TABLE 3

Inhibition by E5 of the fall in blood pressure and intragastric pressure induced by duodenal distension in the anaesthetised rat

| Time (min) after administration of E5 10 μg/kg | % Inhibition of fall in blood pressure (n = 9) | % Inhibition of fall in intragastric pressure (n = 8) |
|---|---|---|
| 5 | 36 ± 15* | 16 ± 5 |
| 10 | 41 ± 18 | 63 ± 14*** |

TABLE 3-continued

Inhibition by E5 of the fall in blood pressure and intragastric pressure induced by duodenal distension in the anaesthetised rat

| Time (min) after administration of E5 10 µg/kg | % Inhibition of fall in blood pressure (n = 9) | % Inhibition of fall in intragastric pressure (n = 8) |
|---|---|---|
| 15 | 37 ± 22 | 51 ± 14** |
| 20 | 32 ± 19 | 47 ± 17* |

*P < 0.05;
**P < 0.01;
***P < 0.005
Student's 't' test

We claim:

1. A method of treatment of visceral pain in mammals, including humans, which method comprises the administration to the mammal in need of such treatment, a visceral pain relieving effective amount of a compound of formula (I) or a pharmaceutically acceptable salt thereof:

$$X-CO-Y-Z \quad (I)$$

wherein

X is a group of formula (d) or (e):

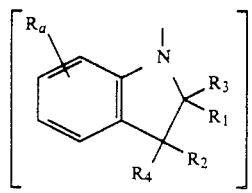 (a)

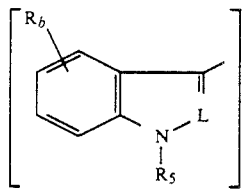 (b)

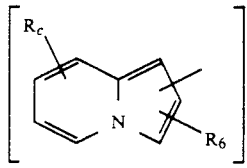 (c)

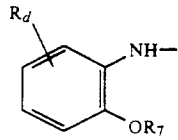 (d)

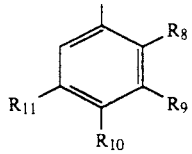 (e)

wherein
$R_d$ is selected from hydrogen, halogen or hydroxy;
$R_7$ is independently hydrogen or $C_{1-6}$ alkyl;
either $R_8$ is $C_{1-6}$ alkoxy;
$R_9$ is hydrogen;
$R_{10}$ is amino or $C_{1-7}$ alkanoylamino; and
$R_{11}$ is halo or $C_{1-6}$ alkylthio; or
$R_8$ is hydrogen;
$R_9$ is halo $C_{1-6}$ alkoxy or $C_{1-6}$ alkyl;
$R_{10}$ is hydrogen or $C_{1-6}$ alkoxy; and
$R_{11}$ is halo, $C_{1-6}$ alkoxy or $C_{1-6}$ alkyl;
Y is NH or O, with the proviso that Y is NH when X is (e) and $R_8$ is $C_{1-6}$ alkoxy;
Z is a group of formula (f), (g) or (h):

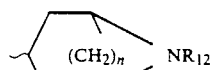 (f)

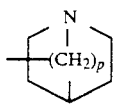 (g)

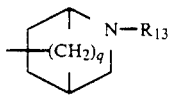 (h)

wherein
n is 2 or 3;
p and q are independently 1 to 3; and
$R_{12}$ or $P_{13}$ is methyl or ethyl.

2. A method according to claim 1 wherein Z is of sub-formula (f) as defined in claim 1, and n is 2 or 3.

* * * * *

UNITED STATES PATENT AND TRADEMARK OFFICE
CERTIFICATE OF CORRECTION

PATENT NO. : 5,063,231

DATED : November 5, 1991

INVENTOR(S) : Gareth J. Sanger and Helen E. Marr

It is certified that error appears in the above-identified patent and that said Letters Patent is hereby corrected as shown below:

On the title page, Item [30] Foreign Application Priority Data
January 19, 1987 [GB]   United Kingdom ............8701022

Signed and Sealed this

Thirtieth Day of March, 1993

*Attest:*

STEPHEN G. KUNIN

*Attesting Officer*          *Acting Commissioner of Patents and Trademarks*

UNITED STATES PATENT AND TRADEMARK OFFICE
CERTIFICATE OF CORRECTION

PATENT NO. : 5,063,231

DATED : November 5, 1991

INVENTOR(S) : Gareth J. Sanger and Helen E. Marr

It is certified that error appears in the above-identified patent and that said Letters Patent is hereby corrected as shown below:

Column 7,     Claim 1, after line 9, delete

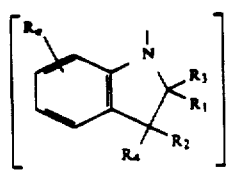 (a)

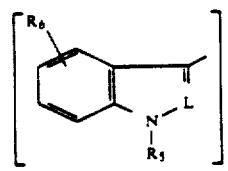 (b)

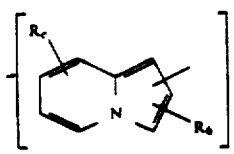 (c)

and in the last line, change "P$_{13}$" to --R$_{13}$--.